US012628817B2

(12) United States Patent
Arnoult et al.

(10) Patent No.: US 12,628,817 B2
(45) Date of Patent: *May 19, 2026

(54) METHOD FOR INCREASING THE LIFESPAN AND MOTILITY OF ANIMAL SPERM USING AN INHIBITOR OF Slo3 POTASSIUM CHANNEL

(71) Applicants:IMV TECHNOLOGIES, Saint Ouen sur Iton (FR); UNIVERSITE GRENOBLE ALPES, Saint Martin d'Heres (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); SWISSGENETICS, Zollikofen (CH)

(72) Inventors: Christophe Arnoult, Saint Etienne de Crossey (FR); Eric Schmitt, Villaines-la-Juhel (FR); Guillaume Martinez, Poisat (FR); Jessica Escoffier, Saint Etienne de Crossey (FR)

(73) Assignees: IMV TECHNOLOGIES, Saint Ouen sur Iton (FR); UNIVERSITE GRENOBLE ALPES, Saint Martin d'Heres (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); SWISSGENETICS, Zollikofen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/322,906

(22) Filed: May 24, 2023

(65) Prior Publication Data

US 2023/0292743 A1      Sep. 21, 2023

Related U.S. Application Data

(62) Division of application No. 16/955,539, filed as application No. PCT/EP2018/085673 on Dec. 18, 2018, now Pat. No. 11,696,579.

(30) Foreign Application Priority Data

Dec. 18, 2017     (EP) ..................................... 17306818

(51) Int. Cl.
| | |
|---|---|
| *A01N 1/126* | (2025.01) |
| *A01N 1/125* | (2025.01) |
| *A61D 19/02* | (2006.01) |
| *A61K 31/14* | (2006.01) |
| *A61K 31/4748* | (2006.01) |

(52) U.S. Cl.
CPC ............. *A01N 1/126* (2025.01); *A01N 1/125* (2025.01); *A61D 19/024* (2013.01); *A61D 19/027* (2013.01); *A61K 31/14* (2013.01); *A61K 31/4748* (2013.01)

(58) Field of Classification Search
CPC ...... A01N 1/126; A01N 1/125; A61D 19/024; A61D 19/027; A61K 31/14; A61K 31/4748
See application file for complete search history.

(56) References Cited

U.S. PATENT DOCUMENTS

| | | | |
|---|---|---|---|
| 6,815,539 | B1 | 11/2004 | Salkoff et al. |
| 2004/0031071 | A1 | 2/2004 | Morris et al. |

FOREIGN PATENT DOCUMENTS

| | | | |
|---|---|---|---|
| FR | | 995878 A | 12/1951 |
| GB | | 669265 A | 4/1952 |
| WO | WO 2012/074060 | * | 6/2012 |
| WO | 2016026843 A1 | | 2/2016 |

OTHER PUBLICATIONS

Yeung et al. (Molecular Human Reproduction 7(9) 819-828 (2001).*
Curry (cryopreservation and Freeze drying Protocols (2007).*
Santi et al., "The SLO3 sperm-specific potassium channel plays a vital role in male fertility", FEBS Letters, pp. 1041-1046, vol. 584, No. 5 (Mar. 2010).

(Continued)

*Primary Examiner* — Shirley V Gembeh
(74) *Attorney, Agent, or Firm* — FisherBroyles, LLP; Roger L. Browdy; James E. Mrose

(57) ABSTRACT

The invention relates to a method for increasing the lifespan of animal sperm comprising contacting said sperm with an inhibitor of Slo3 potassium channel.

The invention also relates to a use of an inhibitor of Slo3 potassium channel, for increasing the lifespan of animal sperm or motility of capacitated animal sperm, comprising contacting an inhibitor of Slo3 potassium channel with said sperm. Moreover, the invention relates to an artificial insemination instrument for use in artificial insemination of an animal, comprising animal sperm in contact with an inhibitor of Slo3 potassium channel.

The invention also relates to a method for artificially inseminating an animal using said artificial insemination instrument.

Eventually, the invention relates to a method for increasing the fertility of an animal, comprising contacting sperm of said animal with an inhibitor of Slo3 potassium channel; then artificially inseminating said animal with said sperm.

3 Claims, 5 Drawing Sheets

(56) References Cited

OTHER PUBLICATIONS

Brenker et al., "The calcium activated potassium current of human sperm is mediated by Slo3", ELIFE, pp. 1-19 (Jan. 2014).

Navarro et al.,"Ion channels that control fertility in mammalian spermatozoa", International Journal of Developmental Biology, pp. 607-613, vol. 52, No. 5-6 (Jan. 2018).

Betsy Navarro et al: "KSper, a pH-sensitive K + current that controls sperm membrane potential", Proceedings of the National Academy of Sciences (PNAS), vol. 104, No. 18, May 1, 2007 (May 1, 2007), pp. 7688-7692.

Polina V. Lishko et al: "The Control of Male Fertility by Spermatozoan Ion Channels", Annual Review of Physiology., vol. 74, No. 1, Oct. 13, 2011 (Oct. 13, 2011), pp. 453-475.

Yeung et al., Effects of the ion-channel blocker quinine on human sperm volume, kinematics and mucus penetration, and the involvement of potassium channels, (Molecular Human Reproduction, 7(9)819-828 (2001).

Wrighton et al., Mechanism of inhibition of mouse Slo3 (Kca5* 1) potassium channels by quinine, quinidine and parium, (British J. of Pharmacology(2015) 172: 4355-4363).

Curry, Cryopreservation of Manmalian Semen, (cryopreservation and Freeze-Drying Protocols pp. 303-311 (2007).

Geng et al., A genetic variant of the sperm-specific SL03 K+ channel has altered pH and Ca2+ sensitivities, JBC (2017) 292(21)8978-8987.

Torre ML et al., "Boar semen controlled delivery system: storage and in vitro spermatozoa release", Journal of Controlled Release, 85(1), pp. 83-89, DOI:10.1016/S0168-3659(02)00290-0, Dec. 13, 2002.

* cited by examiner

% of 2-cell embryos at 48 hours post fertilization

Incubation duration, hours control
5 µM clofilium

% of 2-cell embryos at 24 hours control
0.2 µM clofilium

% of 2-cell embryos at 24 hours control
5 µM clofilium

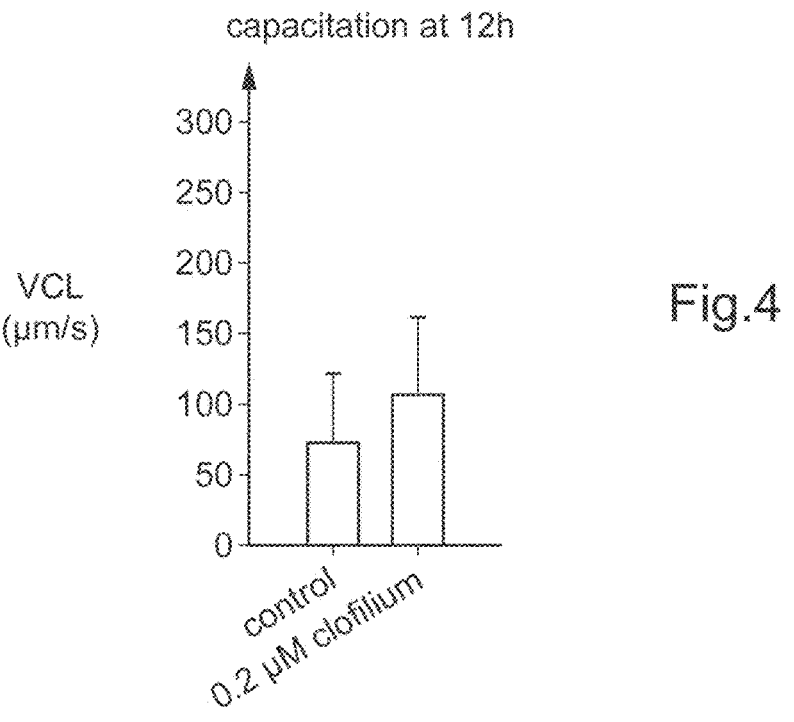
Fig.4
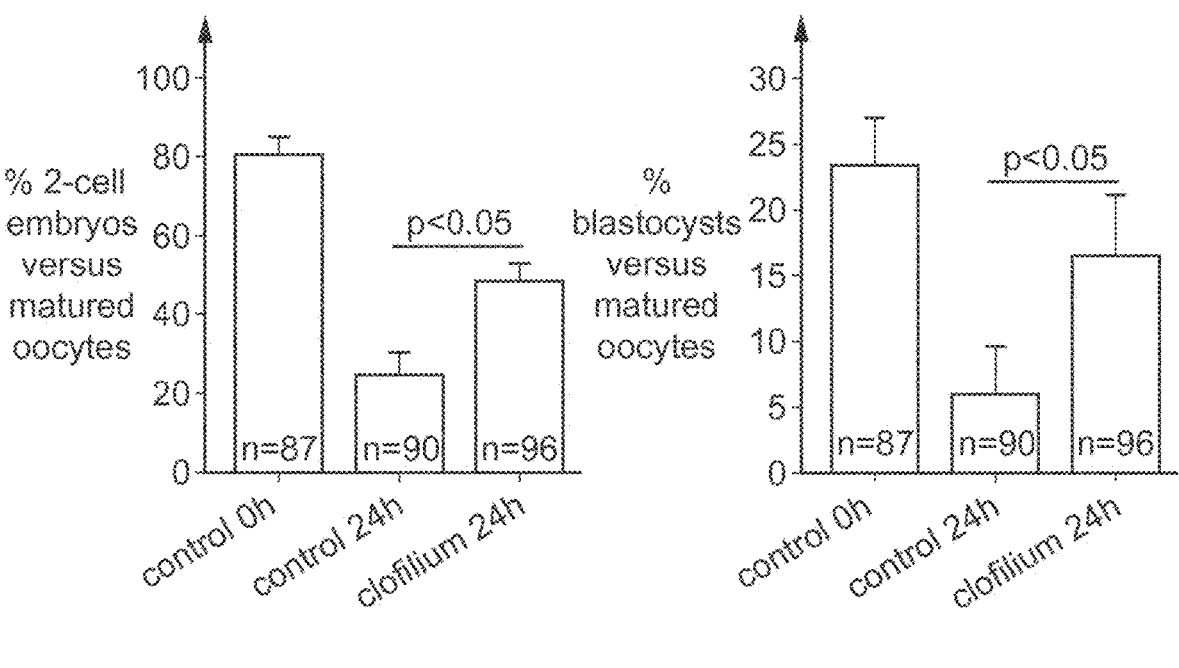
Fig.5A
Fig.5B

*p<0.05 versus [0 μM]
paired t-test
n=7
[0.2] p-value = 0.03
[0.5] p-value = 0.003
[1] p-value = 0.12
[5] p-value = 0.14

*p<0.05 versus [0 μM]
paired t-test
n=7
[0.2] p-value = 0.01
[0.5] p-value = 0.12
[1] p-value = 0.09
[5] p-value = 0.55

METHOD FOR INCREASING THE LIFESPAN AND MOTILITY OF ANIMAL SPERM USING AN INHIBITOR OF Slo3 POTASSIUM CHANNEL

FIELD OF THE INVENTION

The present invention relates to increasing the lifespan of animal (i.e. non-human) sperm. The invention also relates to increasing the motility of animal sperm, in particular of capacitated sperm. The invention also relates to an artificial insemination instrument for use in artificial insemination of an animal, a method for artificially inseminating an animal, as well as a method for increasing the fertility of an animal.

BACKGROUND OF THE INVENTION

Prevalence of artificial insemination (AI) is nearly 100% in dairy cattle reproduction, where sperm is deposited into the vaginal tract or uterus of the female, in order to increase the use of male semen of high genetic value. However, the conception rate of cattle to artificial insemination has decreased for the last twenty years. A major factor contributing to the low conception rate is the impossibility to ascertain the timing of ovulation.

When conception fails, artificial insemination (AI) needs to be repeated, for example on the female cattle, which imposes a burden on farmers. Thus, there is a need for an artificial insemination method with enhanced conception rate. Freezing of sperm is often necessary in artificial reproduction technologies, in particular for bovine sperm. For artificial insemination of livestock, frozen semen aliquoted in semen straws and preserved in liquid nitrogen is usually used. A semen straw for cryopreservation is generally prepared by diluting semen in at least one diluent (usually in a primary diluent and then in a secondary diluent, which is generally the primary diluent supplemented with the cryoprotectant agent). Straws are filled with this diluted semen, and frozen.

Spermatozoa (sperm) are cells and thus are sensitive to freezing. At least one cryoprotectant must be added to the diluent in order to prevent cell death. Glycerol, sugars (glucose, fructose, lactose and raffinose) and lipids (egg yolk or synthetic lipids) are usually used as cryoprotectants for improving the survival rate and the fertilization ability of the spermatozoa after freezing and thawing. Despite the use of cryoprotectants in diluents, freezing usually impacts negatively sperm viability. Indeed, spermatozoa that have been previously frozen, once thawed, have a reduced motility compared to fresh sperm samples. Cryopreservation leads to the decrease of sperm motility, viability and lifespan. Agents activating motility and/or preserving motility, in particular after freezing, can positively impact the success rate of artificial reproduction in numerous species, like horses, pigs, cattle, and poultry (for example, turkeys).

Another drawback of the freezing process is an acceleration of the maturation process of sperm, known as capacitation. Capacitation is a necessary step of maturation, normally occurring in the female tract. Although necessary, capacitation leads to irreversible sperm changes and eventually to damages decreasing semen quality, motility and ability to fertilize an oocyte. Capacitation is associated with a strong increase of the metabolic activity and decreases the overall lifespan of sperm within the female reproductive tract. This is particularly damaging when insemination is not synchronized with ovulation.

Thus there is a need for agents that can increase the conception rate for use in industrial artificial insemination procedures of animals (in particular mammals and birds, more particularly domestic mammals and poultry), in particular when the artificial insemination requires the freezing of sperm.

SUMMARY OF THE INVENTION

The inventors have discovered that inhibitors of Slo3 potassium channel, in particular barium, mibefradil, clofilium and/or quinidine, more particularly clofilium and/or quinidine, may be used to increase the lifespan of animal sperm.

This leads to an increase of storage time of the sperm, and to an improvement of the sperm ability to fertilize after a long period (e.g. 24 h or 48 h) of capacitation. According to the invention, the motility of capacitated sperm is surprisingly increased, in particular after a long period (e.g. 24 h or 48 h) of capacitation. The increase of the lifespan of sperm makes it possible that sperm, in particular capacitated sperm, introduced before ovulation, remain alive longer in the female reproductive tract and exhibit motility and ability to fertilize an oocyte in the ovulation site at the ovulation date of the female e.g. the cow, thereby making it possible to enhance the conception rate of an animal population.

The invention thus relates to a method for increasing the lifespan of animal sperm comprising contacting said animal sperm with an inhibitor of Slo3 potassium channel.

The invention also relates to a method for increasing the motility of capacitated animal sperm comprising contacting said capacitated animal sperm with an inhibitor of Slo3 potassium channel.

The invention also concerns the non-therapeutical use of an inhibitor of Slo3 potassium channel for increasing the lifespan of animal sperm, comprising contacting an inhibitor of Slo3 potassium channel with said animal sperm.

The invention also concerns the non-therapeutical use of an inhibitor of Slo3 potassium channel for increasing the motility of capacitated animal sperm, comprising contacting an inhibitor of Slo3 potassium channel with said capacitated animal sperm.

The invention also concerns an artificial insemination instrument for use in artificial insemination of an animal, comprising animal sperm in contact with an inhibitor of Slo3 potassium channel. Said artificial insemination instrument is preferably a semen straw for cryopreservation.

The invention also concerns a method for artificially inseminating an animal, comprising the use of said artificial insemination instrument.

The invention also concerns a method for increasing the fertility of an animal, comprising the following successive steps:

a) Contacting sperm of said animal with an inhibitor of Slo3 potassium channel;

b) Artificially inseminating said animal with the sperm issued from step a).

DETAILED DESCRIPTION OF THE INVENTION

Slo3 potassium channel is known as a key potassium channel involved in capacitation. Genetic deletion of Slo3 leads to male infertility and inhibitors of Slo3 potassium channel are known as fertilization blockers, by preventing sperm hyperpolarization and $Ca^{2+}$ influx occurring during capacitation, two events known to be necessary for sperm fertility competence.

As a result of intensive research carried by the inventors on the survival of spermatozoa filled in straws for artificial insemination and on the ability to fertilize and the motility of animal sperm, in particular of capacitated sperm, the present inventors have found that the lifespan of animal sperm and motility of capacitated animal sperm can be surprisingly enhanced when a straw for artificial insemination was prepared comprising the semen in contact with an inhibitor of Slo3 potassium channel. The lifespan of animal sperm can also be surprisingly enhanced when freshly ejaculated semen is in contact with an inhibitor of Slo3 potassium channel. The motility of animal capacitated sperm can also be surprisingly enhanced when freshly ejaculated sperm is put in contact with an inhibitor of Slo3 potassium channel and capacitated in a capacitating medium containing an inhibitor of Slo3 potassium channel.

The invention also relates to increasing the fertility of an animal in animal production methods, including artificial insemination methods in which the sperm is in contact with an inhibitor of Slo3 potassium channel.

In the present invention, the term "A and/or B" means "A", or "B", or "A and B". In the present invention, a "capacitation medium" is a medium in which spermatozoa can undergo capacitation.

In the present invention, a "freezing medium" (or protective medium) is a medium which protects cells from damages caused by freezing. A freezing medium usually contains at least one cryoprotectant agent. The freezing medium is generally comprised within an artificial insemination instrument.

In the present invention, a "maturation medium" is a medium which supports the maturation of oocytes from stage GV (Germinal Vesicle) to stage MII (Metaphase II). Oocytes at stage MII are "mature oocytes".

In the present invention, a "fertilizing medium" means a medium, usually a solution, comprising capacitated sperm and matured oocytes.

According to the invention, "increasing the lifespan of sperm" means that the percentage of sperm population having a fertilizing capacity is increased after a certain incubation time when the inhibitor of Slo3 channel is used in a medium containing the sperm at about 37° C., when compared to the case where no such inhibitor is used, all other things remaining equal, without damaging the ability to fertilize of the sperm population.

The incubation time varies in function of the targeted species. For most of the species, 12 h is sufficient to observe the technical effect.

This is measured by the percentage of 2-cell embryos produced after fertilization of mature oocytes, when the incubation of sperm prior to fertilization was made in a capacitation medium (such as the one exemplified below: Sp-TALP capacitation medium) at about 37° C. Accordingly, it corresponds to an increase within a range respectively of 10% to 60% at 24 h incubation time (e.g. 30%) and of 10% to 50% at 48 h incubation time (e.g. 45%).

According to the invention, "increasing the motility of capacitated sperm" means that the total motility of the capacitated sperm population, expressed in percentage, is increased after a certain incubation time when the inhibitor of Slo3 channel is used in a medium containing the sperm at about 37° C., with respect to the case where no such inhibitor is used, all other things remaining equal.

This is measured by incubation in a capacitation medium (such as the one exemplified below: Sp-TALP capacitation medium) for 24 h at about 37° C. Accordingly, it corresponds to an increase within a range of 100% to 500% (e.g. 400%).

In other words, the presence of an inhibitor of Slo3 potassium channel in a medium containing the sperm, all other things remaining equal, increases the motility of capacitated sperm.

For the definitions above, the medium containing the sperm is usually a preservative medium or a protective medium. This is e.g. a freezing medium or a capacitation medium.

In the present invention, the term "motility" is the ability of sperm to move spontaneously and actively, consuming energy in the process. For spermatozoa, this is a swimming-like-motion made by the regular beat of their flagellum, that is to say a flagellar motility.

In the present invention, the term "capacitation" means the maturation of animal spermatozoa which is required to render them competent to fertilize an oocyte (once undergone this final maturation step, sperm penetrate the surrounding protective layers of the oocytes, which involves the acrosome reaction). A capacitation period is a period during which the capacitation takes place. A capacitation period can possibly last after the capacitation takes place. According to the invention, "capacitated sperm" means sperm incubated for a minimum period of time in a capacitation medium. This period of time varies in function of the targeted species (for instance it is generally about 45 min for mouse and about 4 hours for bovine). Capacitation medium usually contains bovine serum albumin for mouse sperm, and bovine serum albumin and heparin for bovine sperm.

As it is known to the skilled person, capacitation leads to changes in sperm motility pattern, which are measurable with a CASA system, and phosphorylation of protein in their tyrosine residues, which is measurable in Western Blot.

For example, according to the invention, sperm capacitation is measured with antiphosphotyrosine Western blot as described in "*Capacitation of mouse spermatozoa. I. Correlation between the capacitation state and protein tyrosine phosphorylation*. Visconti P E et al, Development. 1995 April; 121(4):1129-37". In brief, washed sperm were resuspended in Laemmli sample buffer without β-mercaptoethanol, and boiled for 5 minutes. After centrifugation, 5% β-mercaptoethanol was added to the supernatants, and the mixture was boiled again for 5 minutes. Protein extracts equivalent to $1-2 \times 10^6$ sperm were loaded per lane and subjected to SDS-PAGE. Resolved proteins were transferred onto polyvinylidene difluoride membranes (Millipore). Membranes were treated with 20% fish skin gelatin (Sigma) in PBS-T, then incubated for one hour at room temperature with anti-Phosphotyrosine Antibody (clone 4G10, Millipore) (1:10,000); this was followed by 1 h of incubation with a horseradish peroxidase labelled secondary antibody. Immunoreactivity was detected using chemiluminescence detection kit reagents and a Chimidoc™ Station (Biorad). According to the invention, "contacting" means "put in contact with". Preferably, contacting is mixing.

In the present invention, the term "conception rate" means a measure of the animal fertility. It is usually calculated by dividing the number of pregnant females by the total number of inseminations.

According to the invention, animals are preferably mammals and birds, more preferably domestic mammals and poultry.

In the present invention, the inhibitor of Slo3 potassium channel is generally to be used in effective amount. The term "effective amount" refers to the amount sufficient to induce a desired biological result. Here, the result is lifespan or motility sperm increase. The "effective amount" depends on the inhibitor of Slo3 potassium channel. It is generally as follows:

0.5 to 5 mM, preferably 1 to 2.5 mM, more preferably 1.5 to 2.5 mM, when the inhibitor of Slo3 potassium channel is barium;

1 to 100 mM, preferably 10 to 30 mM, more preferably 15 to 25 mM, when the inhibitor of Slo3 potassium channel is mibefradil;

0.1 to 50 μM, preferably 0.1 to 5 μM, more preferably 0.2 to 1 μM, when the inhibitor of Slo3 potassium channel is clofilium;

0.1 to 50 μM, preferably 5 to 30 μM, more preferably 20 to 30 μM, when the inhibitor of Slo3 potassium channel is quinidine.

This molar concentration is generally calculated or inferred from the total volume of the freezing medium or capacitation medium, which is in the form of droplets. According to the invention, the artificial instrument preferably comprises a freezing medium and sperm. This freezing medium comprises the inhibitor of Slo3 potassium channel. Preferably these constituents have been mixed all together.

Barium is a salt of barium such as barium chloride or barium sulfate. Barium sulfate, which is known as radio-contrast agent, is the inorganic compound with the chemical formula $BaSO_4$, CAS number 7727-43-7.

Mibefradil is mibefradil dichloride, the current name of (1S,2S)-2-(2-((3-(1H-benzo[d]imidazol-2-yl)propyl) (methyl)amino)ethyl)-6-fluoro-1-isopropyl-1,2,3,4-tetrahy-dronaphthalen-2-yl 2-methoxyacetate, known under the trade name Posicor from Roche, CAS number 116644-53-2. It is known as antihypertensive agent and anti-chronic angina pectoris agent.

Clofilium is the current name of 4(-4(Chlorophenyl)butyl-diethyl-heptylammonium (IUPAC name), CAS number 68379-02-2. It is known as an antiarrhythmic agent (class III).

Quinidine is the current name of (9S)-6'-methoxycincho-nan-9-ol (IUPAC name), CAS number 56-54-2. It is known as an antiarrhythmic agent (class Ia).

The preferred embodiments according to the invention comprise at least one of the following features:

the animal sperm is chosen from bovine, porcine, ovine, birds, such as chickens and turkeys, equine, goat and pets, such as cats and dogs, sperm;

the inhibitor of Slo3 potassium channel is barium, mibe-fradil, clofilium and/or quinidine, preferably clofilium and/or quinidine, more preferably clofilium;

said contacting is carried out in vitro or in vivo;

said animal sperm has been previously frozen and thawed, or has been freshly ejaculated, or recovered from the epididymis, or from the testis.

The invention also relates to the use of an inhibitor of Slo3 potassium channel, for increasing the lifespan of animal sperm, comprising contacting an inhibitor of Slo3 potassium channel with said animal sperm.

The invention also relates to the use of an inhibitor of Slo3 potassium channel, for increasing the motility of capacitated animal sperm, comprising contacting an inhibitor of Slo3 potassium channel with said capacitated animal sperm.

The invention also relates to a method for artificially inseminating an animal, comprising the use of the artificial insemination instrument according to the invention.

According to preferred embodiments of the method for increasing the fertility of an animal according to the invention, said contacting step is carried out in a female by admin-istering inhibitor of Slo3 potassium channel composi-tion in vaginal tract and/or cervical of said female, and said artificially inseminating step is an insemination of said female by said animal sperm; and/or said contacting step is carried out in a male preferably by injection into the epididymis or testis of said male, and said artificially inseminating step is an insemination of a female by said animal sperm; and/or said artificially inseminating step is carried out by the use of an artificial inseminating instrument; and/or said artificially inseminating step is carried out by the use of a semen straw for cryopreservation.

The freezing medium within the straw of the present invention preferably comprises generally suitable additives, known to the skilled person, such as at least one cryopro-tectant agent such as alcohols (glycerol, propanediol), alde-hydes (formamide), sugars (sucrose, raffinose, trehalose) or dimethylsulphoxide (DMSO) and a diluent such as egg yolk, milk proteins or sugar.

The inhibitor of Slo3 potassium channel may be admin-istered by routes that allow the inhibitor to come into contact with sperm, in dosage forms appropriate for each route of administration such as a solution, suspension, gel, cream, milk, capsule, tablet and/or other suitable forms for admin-istration to animals.

For example, according to an embodiment of the inven-tion, the inhibitor of Slo3 potassium channel is administered to females by the vaginal route in any suitable form, including creams or gels, preferably in the form of a suppository.

The techniques of the present invention will be readily understood by considering the accompanying drawings.

Figures 1, 2, 3A, 3B:
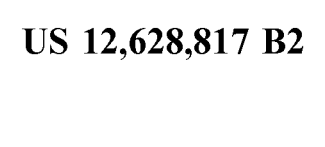
FIG. 1 is a schematic partial illustration of an artificial inseminating instrument 10 according to the invention.
FIG. 2 is a schematic diagram illustrating the impact of clofilium in a mouse sperm capacitation medium, by show-ing the percentage of 2-cell embryos versus (vs) mature oocytes at 48 h post fertilization with regard to the incuba-tion time of sperm prior fertilization (in hours, h) for each of the two solutions tested (control and 5 μM solution of clofilium).

FIGS. 3A and 3B comprise two schematic diagrams, respectively, illustrating the impact of clofilium in a mouse sperm capacitation medium prior fertilization (12 hours incubation), by showing the percentage of 2-cell embryos vs mature oocytes at 24 h post fertilization obtained for each of the solutions tested (control and clofilium), respectively for a 0.2 μM solution of clofilium (FIG. 3A) and for a 5 μM solution of clofilium (FIG. 3B).

FIG. 4 is a schematic diagram illustrating the percentage of motility (in terms of VCL, in μm/s) in a mouse sperm capacitation medium prior fertilization (12 hours incuba-tion) by showing the motility of each of the solution tested (control and 0.2 μM clofilium).

FIGS. 5A and 5B comprise two schematic diagrams, respectively, illustrating respectively the impact of clofilium in a bovine sperm capacitation medium prior fertilization (24 hours incubation), by showing the percentage of bovine 2-cell embryos vs matured oocytes at 48 h post fertilization (FIG. 5A) and the percentage of bovine blastocysts versus matured oocytes measured 9 days post fertilization (FIG. 5B), in both cases for each of the solutions tested (control 0 h, control 24 h, clofilium 24 h).

Figure 6A:
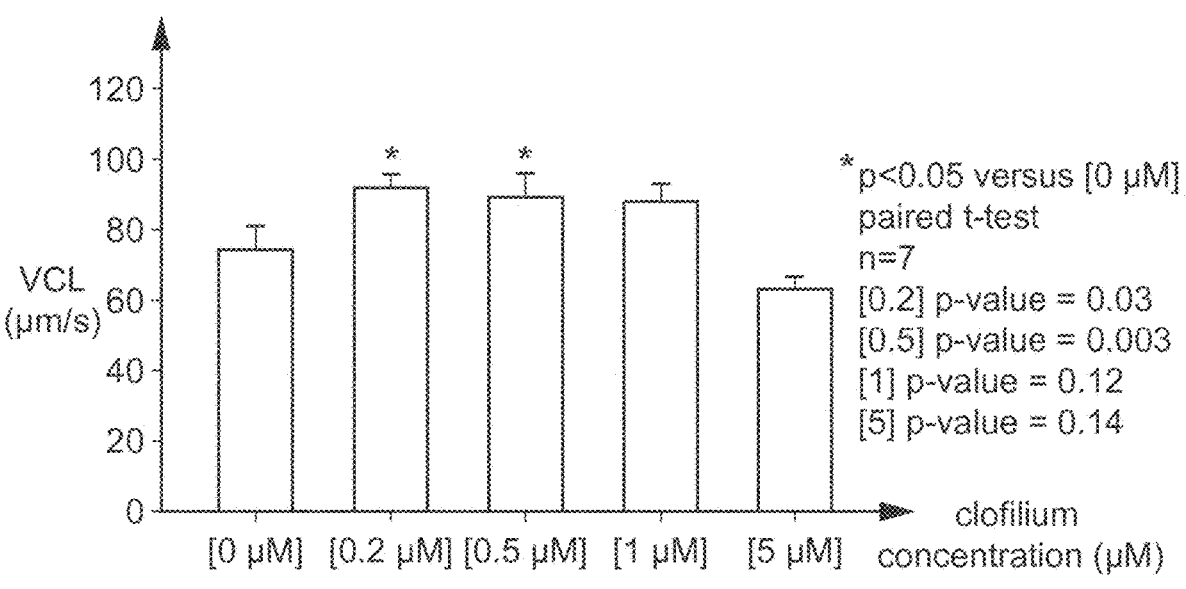
Figure 6B:
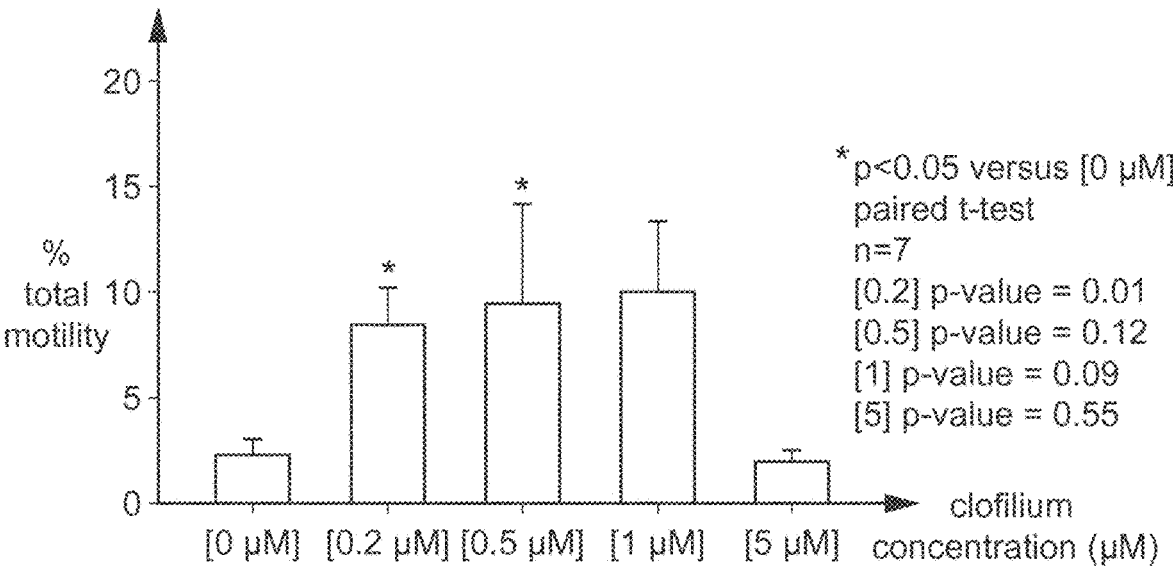

FIGS. 6A and 6B comprise comprises two schematic diagrams, respectively, illustrating respectively the impact of clofilium on bovine sperm motility (in terms of VCL, in μm/s), sperm being incubated 24 h in a capacitation medium prior CASA evaluation, for each of the solutions tested (control, 0.2 μM clofilium, 0.5 μM clofilium, 1 μM clofilium and 5 μM clofilium) (FIG. 6A) and the total motility (%), for each of the solutions tested (control, 0.2 μM clofilium, 0.5 μM clofilium, 1 μM clofilium and 5 μM clofilium) (FIG. 6B).

Figure 7:
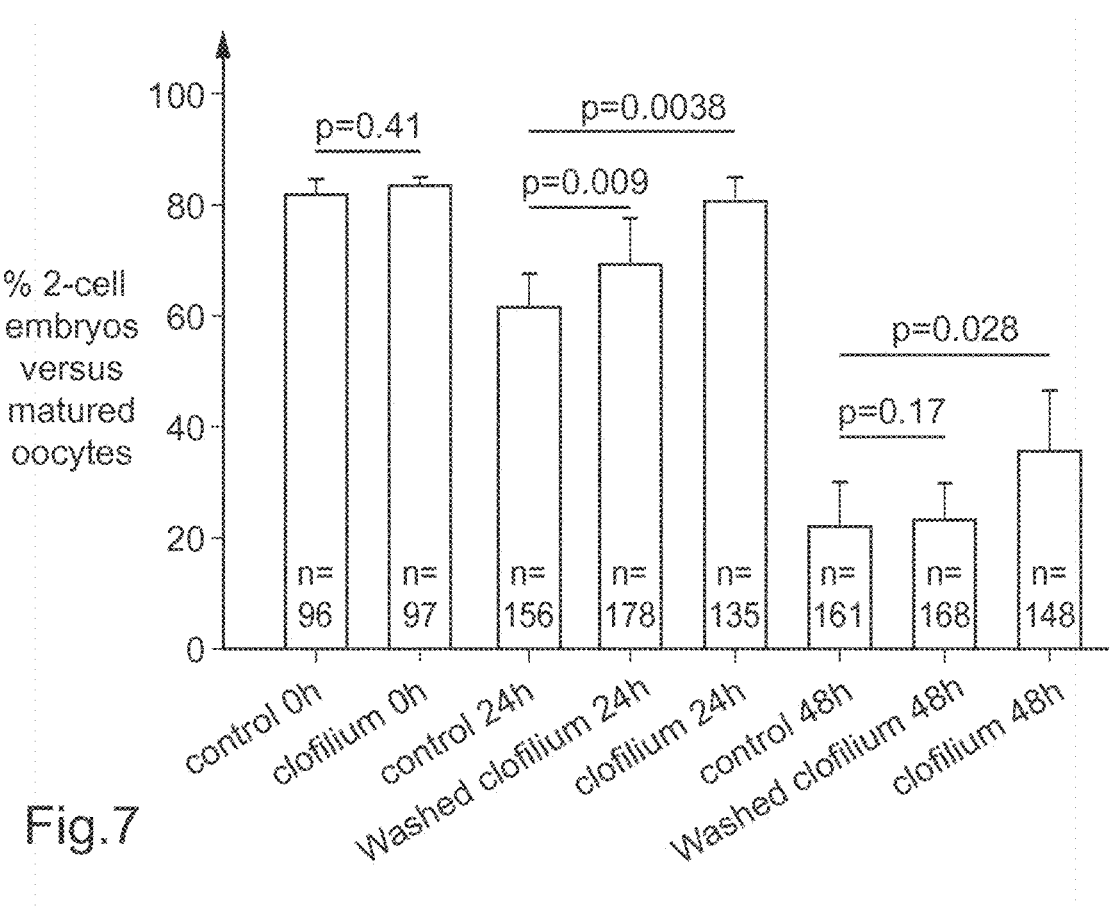

FIG. 7 is a schematic diagram illustrating the impact of washing clofilium on the percentage of 2-cell embryos vs matured oocytes at 24 h post fertilization by bovine sperm. Bovine sperm were frozen with a control medium ("control") or a medium containing 0.2 μM clofilium ("clofilium"), thawed and used either immediately ("0 h"), 24 hours later ("24 h") or 48 h later ("48 h") for fertilization. Two conditions were tested: after thawing sperm were centrifuged and diluted with either a control solution ("washed clofilium") or a solution containing 0.2 μM clofilium ("clofilium").

Figure 8:
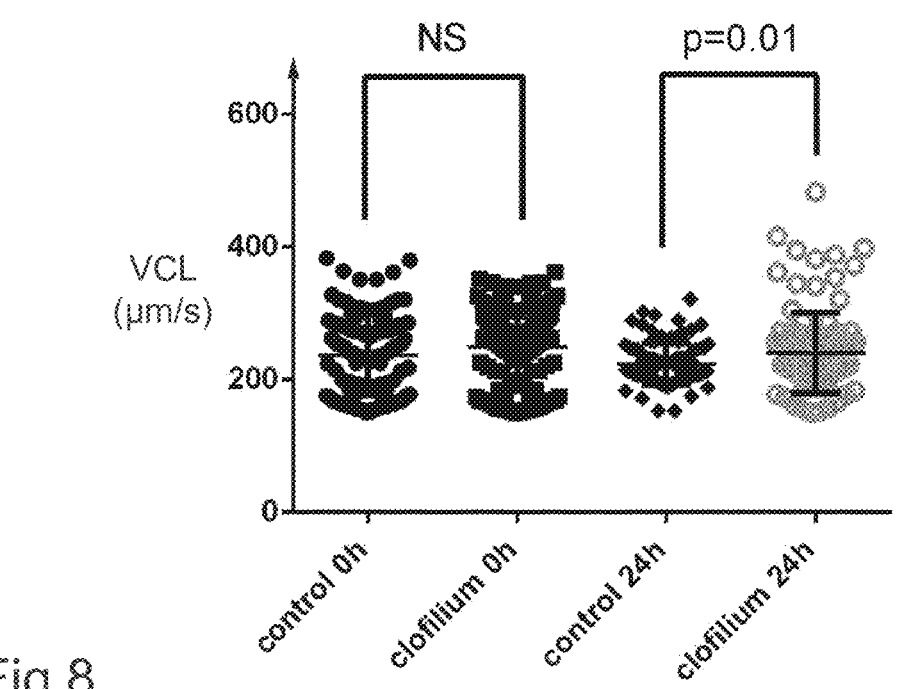

FIG. 8 is a schematic diagram illustrating the impact of clofilium on bovine sperm motility (in terms of VCL, in μm/s), the sperm presenting a sufficient velocity (VCL>150 μm/s), sperm being incubated 0 h or 24 h in a capacitation medium prior CASA evaluation, for each of the solutions tested (control or 0.2 μM clofilium).

Figure 9:
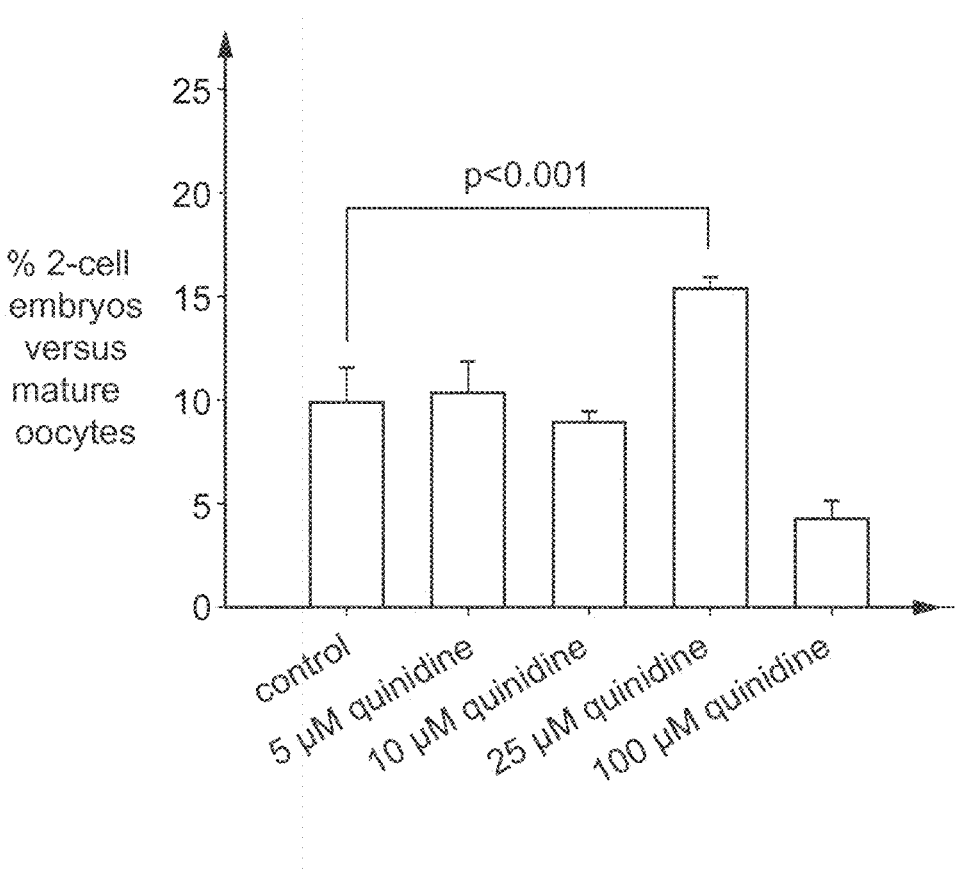

FIG. 9 is a schematic diagram illustrating the impact of quinidine in a capacitation medium (12 hours incubation), by showing the percentage of 2-cell embryos vs mature oocytes at 24 h post fertilization by mouse sperm for each of the solutions tested (control, 5 μM quinidine, 10 μM quinidine, 25 μM quinidine and 100 μM quinidine).

FIG. 1 is a diagrammatic view in longitudinal cross-section of a straw 10 for the preservation of a predetermined dose of liquid-based substance, in particular diluted animal semen.

The straw 10 comprises a container which is a tube 11 and a stopper 12. It is used for the artificial insemination of livestock, in particular bovine.

The tube 11 is conventionally made from extruded plastic material, with an inside diameter for example of 1.6 or 2.5 mm and a length of the order of 133 mm.

The tube 11 is a substantially cylindrical sleeve partly filled by the sperm diluted in freezing medium. This tube is capable of being frozen and thawed without changing its properties and without leaching any substances in its content.

The stopper 12 is usually of the three-part type originally described in French patent 995 878, corresponding to British patent 669 265, i.e. formed by two plugs 13 and 14 made from a fibrous substance enclosing a powder 15 which, on contact with a liquid, is capable of transforming into an impermeable paste or gel adhering to the wall of the tube so that the stopper is liquid-tight.

In the initial state, shown in FIG. 1, the stopper 12 is arranged close to the end 16 of the tube 11 and it is provided that in the filled state, the dose of liquid substance which must be preserved in the straw 10 is placed between the stopper 12 and the end 17 of the tube 11 that is the furthest from the stopper 12. In order to fill the straw 10, the end 16 is placed in communication with a vacuum source while the end 17 is placed in communication with a vessel containing the substance to be introduced into the straw.

The air initially contained between the stopper 12 and the end 17 is sucked through the stopper while the substance moves forward in the tube until it encounters the stopper 12, by the end 18 thereof that is turned towards the end 17 of the tube 11, that is to say the end of the stopper 12 that can be seen on the right in FIG. 1.

If necessary, the straw is welded close to one or both of its two ends 16 or 17 and is placed in cold storage.

In order to empty the straw 10, if necessary after cutting the welded end portions and thawing, there is inserted into the tube 11 a rod which comes to bear on the end 19 of the stopper 12 (which end is situated on the opposite side to the end 18). Using this rod, the stopper 12 is made to slide in the manner of a piston towards the end 17 or the end which corresponds after cutting the welded portion, which causes the expulsion of the dose of substance which had been introduced into the straw.

FIGS. 2, 3A and 3B, 4, 5A and 5B, 6A and 6B, 7, 8 and 9 are explained in the following examples.

The invention is further illustrated by the following non-limiting examples, which are given for illustrative purposes only.

EXAMPLES

Example 1: Impact of Clofilium on Mouse Sperm Lifespan and Motility

These tests were conducted on mouse sperm and mature MII oocytes. They are illustrated by FIGS. 2 to 4.

Mouse sperm was obtained by manual trituration of caudae epididymides from male and were allowed to swim in M2 medium (from Sigma) for 10 minutes. The M2 medium composition in g/L is as follows: $CaCl_2$ 0.25; $MgSO_4$ (anhydrous) 0.1649; KCl 0.35635; $K_2HPO_4$ 0.162; $NaHCO_3$ 0.35; NaCl 5.53193; Albumin, Bovine Fraction V 4.0; D-Glucose 1.0; HEPES (for 4-(2-HydroxyEthyl)-1-Piperazine EthaneSulfonic acid)×Na 5.42726; Pyruvic Acid×Na 0.0363; DL-Lactic Acid×Na 2.95).

Sperm were then capacitated in M16 medium (from Sigma) with 2% fatty acid-free BSA (for Bovine Serum Albumin) (named "M16-BSA medium") at 37° C. in a 5% v/v $CO_2$ incubator for different times as specified. M16 medium is a commercial and commonly used medium for in vitro fertilization and culture of preimplantation stage embryos.

The M16 medium composition in g/L is as follows: calcium chloride.$2H_2O$ 0.25137; magnesium sulfate (anhydrous) 0.143276; potassium chloride 0.356349; potassium phosphate monobasic 0.161959; sodium chloride 5.5319304; albumin bovine fraction V 4.0; Glucose 1.0; phenol red.Na 0.01; Pyruvic acid.Na 0.0363 and DL-lactic acid.Na 2.61

Oocytes were collected from mature OF1 females, synchronized with 5 units of pregnant mare serum gonadotrophin (PMSG) and 5 units of human chorionic gonadotrophin (HCG). Cumulus were harvested directly from the ampulla and sperm were injected into the M16 droplets containing the cumulus.

1. The first test related to the ability of mouse sperm to fertilize oocytes when incubated prior fertilization in a capacitation medium containing clofilium with regard to a control medium, which is the same capacitation medium but without clofilium. The capacitation medium was M16-BSA medium.

The control medium was the M16-BSA medium containing the sperm. It was compared to the same medium further including clofilium at a concentration of 5 μM (in the M16-BSA medium containing the sperm).

Sperm was incubated in M16-BSA medium with or without clofilium and then added to M16 droplets containing the cumulus comprising the oocytes. Two-cell embryos were counted at 48 h post insemination (n=3). The number of oocytes reaching the two-cell stage were counted at 48 hours after fertilization.

These results are shown in FIG. 2 which is a schematic diagram showing the percentage of 2-cell embryos vs mature oocytes at 48 h post fertilization with regard to the incubation time (in hours, h) for each of the solutions tested ("ctrl" for "control" and "5 μM clofilium").

At 48 hours, clofilium has a positive effect for short incubation periods (<3 hours) and for long incubation periods (>3 hours), since for both a similar number of oocytes reached the 2-cell stages. For the 3 h incubation period, the percentage of 2-cell stages is not significantly different than that of control. On the other hand, a higher number of 2-cell stages than what was observed with the control was observed with clofilium treatment for long incubation periods (>3 hours).

Because the ability of the sperm in the control solution to fertilize oocyte is minimum at 12 hours, we thus compared in a second test the effect of clofilium for a sperm incubation of 12 h prior fertilization.

2. The second test related to the dose of clofilium to be used for the incubation prior fertilization.

Two different concentrations of clofilium were tested: 0.2 μM of clofilium and 5 μM of clofilium (in the M16-BSA medium containing the sperm).

The sperm incubation time prior fertilization was 12 hours.

The results are shown in FIG. 3A which illustrates the percentage of 2-cell embryos vs mature MII oocytes at 24 h post fertilization obtained for the "control" and for a 0.2 μM solution of clofilium ("0.2 μM clofilium") and in FIG. 3B which illustrates the percentage of 2-cell embryos vs mature MII oocytes at 24 h post fertilization obtained for the "control" and for a 5 μM solution of clofilium ("0.5 μM clofilium").

It can be seen that concentrations as low as 0.2 μM of clofilium improves the mouse in vitro fertilization outcome. It suggested that both concentrations (0.2 μM and 5 μM) are potent.

3. The viability of mouse sperm was determined by the measurement of the sperm motility. The motility analysis was performed using Computer Assisted Semen Analysis (CASA analysis). The CASA analysis was always performed in the examples using a CEROS™, Hamilton Thorne Bioscience, USA. VCL was thus measured.

As known to the skilled person, VCL (for Curvilinear Velocity) is the average velocity of the sperm head through its real path.

For this analysis, samples were diluted at 0.1 $10^6$/mL. The diluted sample was incubated for 12 hours at 37° C. in a capacitation medium of M16-BSA medium, with or without 0.2 μM clofilium.

For the CASA measurement, 10 μL of the sample were placed on a 2X-CEL Slides, 100 mm depth, Leja Products B.V., Netherlands, placed on the heating stage (37° C.) of the CEROS™. A total of 10 automatically selected fields were analyzed.

FIG. 4 is a schematic diagram illustrating the percentage of motility of sperm (in terms of VCL, in μm/s), i.e. the impact of clofilium on sperm velocity, after a period of 12 h of capacitation, for each of the solution tested (control and 0.2 μM clofilium). It was observed that the sperm treated with 0.2 μM clofilium ("0.2 μM clofilium") has a higher velocity than the "control" (i.e. non-treated) sperm.

Example 2: Impact of Clofilium Treatment on Frozen Bovine Sperm Lifespan and Motility These tests were conducted on bovine sperm. They are illustrated by FIGS. 5A, 5B, 6A and 6B. Similar in vitro fertilization experiments as in Example 1 were performed using frozen bovine sperm and in vitro maturated oocytes.
Sperm Preparation and Motility Assessment Bovine sperm was obtained by ejaculation. Ejaculate was diluted 1:1 in Optixcell. After 10 minutes of 34° C. incubation, semen was then diluted to a final concentration of 57 million of spermatozoa/mL in Optixcell. Optixcell is a TRIS citrate buffer containing liposomes extruded from egg yolk lecithins, glycerol and antibiotics described by CEE (Directive 88/407/CEE). Diluted semen was slowly cooled down to 4° C. (3 to 4 h equilibration in a tempered water-bath), 0.25 mL straws were filled and then frozen in a controlled rate freezer at a cooling rate of 5° C./min from 4° C. to −10° C., 40° C./min from −10° C. to −110° C., 15° C./min from −110° C. to −140° C./min. Straws were then stored in liquid nitrogen until in vitro fertilization.

Straws were thawed in a water-bath at 37° C. for 45 s. Each straw was wiped with 70° ethanol before being opened. The 0.25 mL thawed semen of each straw was layered under 4 mL of Sp-TALP capacitation medium in a 15 mL conical tube. The Sp-TALP medium composition in mM is as follows: NaCl (114.0); KCl (3.2); $NaH_2PO_4$ (0.3); Na Lactate 60% (10); $MgCl_2$ (0.5); HEPES (10); $NaHCO_3$ (25); Na Pyruvate (1) and gentamicine 50 μg/mL; adjusted pH 7.4 with 6 mg/mL BSA (Bovine Serum Albumin) and 2 μg/mL heparine.

Sperm was centrifugated and resuspended in 4 mL Sp-TALP capacitation medium with or without clofilium (0.2 μM). sperm was kept at 37° C. under saturated humidity for 0 h or 24 h.

For motility, sperm were incubated with 0.2, 0.5, 1 and 5 μM clofilium diluted in the capacitation medium for 24 hours at 37° C. under saturated humidity. Sperm motility was measured using Computer Assisted Semen Analysis (CASA analysis). The CASA analysis was performed using a CEROS™, Hamilton Thorne Bioscience, USA. VCL (curvilinear velocity) was then measured.
Fertilization Step At the end of the incubation period, sperm were centrifugated and the pellet is resuspended in the 100 μL of the remaining solution in the tube. Sperm concentration was measured and 750 000 sperm cells are injected into a fertilization droplet (500 μL) containing oocytes bathing in fertilization medium. The IVF fertilization medium composition in mM is as follows: NaCl 114.0; KCl 3.2; $NaH_2PO_4$ 0.3; Na Lactate 10.0; $CaCl_2$ 2.0; $MgCl_2$ 0.5; $NaHCO_3$ 25.0; MEM (for Minimum Essential Medium) Amino Acids solution 50× (from Life technologies) 2% vol/vol. IVF medium comprises also 6 mg/mL BSA, 0.2 mM pyruvate, 50 μg/mL gentamycin, 23.5 μg/mL heparin, 20 μM/mL penicillamine, 10 μM hypotaurine and 2 μM/mL epinephrine. Sperm (1.5 M/mL) and cumulus oocyte complexes (COCs) co-culture were performed at 38.5° C. under gaseous atmosphere of 5% v/v $CO_2$ and saturated humidity for 48 h and then fertilization outcome was assessed.
Oocyte Preparation Bovine ovaries were collected within 3 h post-slaughter and brought back to the laboratory in saline solution (0.9%) with antibiotic (kanamycin) cover between 25° C. and 35°

C. Cumulus-oocytes complexes (COCs) were recovered from 2-8 mm antral follicles by manual aspiration using a sterile 18-gauge needle attached to a sterile 5 mL syringe filled with collection medium (1% v/v PVA (Poly(Vinyl Alcohol)), 4.2 mM NaHCO$_3$, 10 mM HEPES, 2 mM glutamine, 50 IU/mL penicillin and 50 µg/mL streptomycin in M199 medium). Only grade 1 and 2 COCs were selected for further processing. Groups of 30 COCs were matured in 4-well plate with 500 µL oocyte maturation medium for 24 h at 38.5° C. in a gaseous atmosphere with 5% CO$_2$ and saturated humidity.

The M199 medium composition in mM is the complex solution referred M0393 from Sigma-Aldrich comprising inorganic salts such as calcium chloride 0.1396 g/L, potassium chloride 0.4 g/L, sodium chloride 8 g/L; amino acids such as L-glutamine 0.1 g/L and L-glutamic acid 0.0668 g/L; vitamins; and other components.

Oocyte maturation medium was a modified M199 medium, comprising M199 medium Earle's salts complex solution from Life Technologies (referred 31150-022) and 2 mM glutamine, 0.2 mM sodium pyruvate, 0.1 mM cysteamine, 50 µg/mL gentamycin, 10% v/v FBS (Fetal Bovine Serum) and 0.2 µg/mL EGF (Epidermal Growth Factor).
Fertilization Assessment and Embryo Development Oocytes were removed from the fertilization wells 24 hours after fertilization, treated by vortexing 2 min to remove cumulus cells and washed 3 times by passing through dishes of collection medium Presumed zygotes were then cultured in 4-well plates with 500 µL embryo culture medium covered with 250 µL equilibrated mineral oil for 24 hours and the number of cleaved oocytes were then measured. Culture medium was 10% RD-mKSOM/aa from Momozawa et al., *Journal of Reproduction and Development*, Vol. 57, No. 6, 681-689, 2011. Cleavage rate assessed at 48 h and blastocyst rate at day 9 post-fertilization.

The RD-mKSOM/aa medium composition in mM is as follows: NaCl 98.6; KCl 2.5; CaCl$_2$ 1.71; KH$_2$PO$_4$ 0.35; MgSO$_4$ 0.2; Na Pyruvate 0.3; Na Lactate 3.0; NaHCO$_3$ 25; HEPES 10.0; L-Glutamine+essential and non-essential amino acids; insulin 5 µg/mL; transferrin 5 µg/mL; Na-Selenite 5 ng/mL; EDTA 10 µM dibekacin sulfate 65 µg/ml supplemented with RD 10% (v/v) and corresponding to mix 1:1 of RPMI and Dubelcoo's MEM.

1. The first test related to the ability of bovine capacitated sperm to fertilize oocytes when incubated prior fertilization for a long period of time in a medium containing 0.2 µM clofilium with regard to a control medium without clofilium. The development of the 2-cell embryos was followed up to the blastocyst stage. The period of sperm incubation prior fertilization was 24 hours.

The medium was the sp-TALP medium supplemented with 6 mg/mL BSA and 2 µg/mL heparin.

Sperm was incubated in sp-TALP medium with or without clofilium for a period of 24 hours and then added to droplets containing oocytes. Two-cell embryos were counted at 48 h post insemination (n=3).

The first results are shown in FIG. 5A which is a schematic diagram illustrating the percentage of bovine 2-cell embryos vs matured oocytes obtained at 48 h post fertilization, for each of the solutions tested: control at 0 h ("control 0 h") (sperm used immediately after thawing), control at 24 h ("control 24 h") (corresponding to sperm incubated in sp-TALP 24 h prior fertilization) and clofilium at 24 h ("clofilium 24 h") (corresponding to sperm incubated in sp-TALP containing 0.2 µM clofilium 24 h prior fertilization).

The second results are shown in FIG. 5B, which is a schematic diagram illustrating the percentage of blastocysts vs matured oocytes obtained 9 days after fertilization, for each of the (same) solutions tested: "control 0 h", "control 24 h" and "clofilium 24 h".

These results show that clofilium improves the yield of bovine blastocysts when fertilization is performed with sperm capacitated for 24 hours.

2. The viability of the capacitated sperm was determined by the measurement of the sperm motility. The motility analysis was carried out as in Example 1.3.

The first results are shown in FIGS. 6A and 6B, which illustrates the motility (in terms of VCL, in µm/s), i.e. the sperm velocity, sperm being incubated 24 h in a capacitation medium prior CASA, for each of the solutions tested: control ("[0 µM]"), 0.2 µM clofilium ("[0.2 µM]"), 0.5 µM clofilium ("[0.5 µM]" or "[0.5]"), 1 µM clofilium ("[1 µM]" or "[1]") and 5 µM clofilium ("[5 µM]" or "[5]") (FIG. 6A) and which illustrates the total motility (%), for each of the solutions tested "[0 µM]", "[0.2 µM]" (or "[0.2]"), "[0.5 µM]" (or "[0.5]"), "[1 µM]" (or "[1]") and "[5 µM]" (or "[5]") (FIG. 6B).

As known to the skilled person, the "total motility" indicates the overall percentage of sperm that are moving in any direction (VAP>1 µm/s).

It was observed that the sperm population treated with 0.2 µM clofilium, 0.5 µM clofilium, or 1 µM clofilium, has a higher velocity than the non-treated (i.e. control) sperm population, for each of the criteria.

Example 3: Impact of Clofilium Added During the Semen Preparation Process and Before the Freezing Process of Bovine Sperm on Lifespan In order to be as close as possible of the possible field usage, sperm were frozen with clofilium prior to test their ability to improve fertilization. Two conditions were tested: in the first one, clofilium was present during the sperm incubation period, and in the second one, sperm was washed to remove clofilium in order to mimic the condition that may occur in the female reproductive tract.

Straws containing clofilium were obtained as described below. Bovine ejaculate was split into two fractions, and diluted 1:1 in either Optixcell (Fraction 1) or Optixcell containing clofilium 0.2 µM (Fraction 2). After 10 minutes of 34° C. incubation, semen was then diluted to a final concentration of 57 million of spermatozoa/ml in Optixcell (Fraction 1) or Optixcell containing clofilium 0.2 µM (Fraction 2). Diluted semen was frozen as described above and stored in liquid nitrogen until in vitro fertilization.

Two types of straws were used: control straws and straws containing clofilium. For straws containing clofilium, two conditions were tested: washed and not washed. The wash medium is a commonly used medium, sp-TALP, for bovine sperm handling and which composition is described above. For "not washed" conditions, sperm were incubated with sp-TALP containing 0.2 µM clofilium.

The protocol of the washing procedure is as follows:
For the control at 0 h (labelled "control 0 h"), after thawing, freezing medium was removed by a first wash with sp-TALP, then a second wash was performed with sp-TALP and finally sperm was injected into the droplets containing maturated oocytes;
For the freezing medium comprising clofilium at 0 h (labelled "clofilium 0 h"), after thawing, freezing medium was removed by a first wash with sp-TALP containing 0.2 µM clofilium, then a second wash was performed with sp-TALP containing 0.2 μM clofilium and finally sperm was injected into the droplets containing maturated oocytes;

For the control at 24 h or 48 h (labelled respectively "control 24 h" or "control 48 h"), after thawing, freezing medium was removed by a first wash with sp-TALP, then a 24 h or 48 h incubation in sp-TALP was performed and finally a second wash with sp-TALP was performed, followed by injection into the droplets containing maturated oocytes;

For the freezing medium comprising clofilium at 24 h or 48 h, after thawing, freezing medium was removed by a first wash with sp-TALP, then a 24 h or 48 h incubation in sp-TALP (labelled "Washed clofilium 24 h" or "Washed clofilium 48 h") or sp-TALP containing 0.2 μM clofilium (labelled "clofilium 24 h" or "clofilium 48 h") was performed and finally a second wash with sp-TALP was performed, immediately followed by injection into the droplets containing maturated oocytes.

The results are shown in FIG. 7, which illustrates the percentage of 2-cell embryos vs matured oocytes at 24 h post fertilization obtained for each both 24 h and 48 h incubation conditions for the different media and process (as explained above).

Two conclusions were drawn from these experiments. First, when clofilium is present, its positive effect on embryo outcome lasted 48 hours. Second, in washing conditions, the positive effect at 24 hours is still present, although lower. At 48 hours of incubation, however, the effect is no longer present.

Example 4: Impact of Clofilium (Added During the Semen Preparation Process and Before the Freezing Process) of Bovine Sperm on Motility of Sperm Subpopulation Presenting a Sufficient Curvilinear Velocity Sperm population exhibits a large diversity concerning their velocity, with a range in between 0 to 400 μm per second. However, only sperm presenting a sufficient velocity are able to cross the protective layers surrounding the egg and thus are competent for fertilizing eggs. To take this into account, sperm presenting a VCL>150 μm/s were selected and their velocity measured at different time (0 h and 24 h) in control condition or in the presence of clofilium.

Sperm were frozen without clofilium (control) and with clofilium prior to test their motility. In the second case, clofilium was present during the sperm incubation period and during the capacitation period.

Control straws (i.e. without clofilium) were obtained as described above in example 2 paragraph on sperm preparation.

Bovine Straws containing clofilium were obtained as described above in Example 3.

Bovine ejaculate was split into two fractions, and diluted 1:1 in either Optixcell (Fraction 1) or Optixcell containing clofilium 0.2 μM (Fraction 2). After 10 minutes of 34° C. incubation, semen was then diluted to a final concentration of 57 million of spermatozoa/ml in Optixcell (Fraction 1) or Optixcell containing clofilium 0.2 μM (Fraction 2). Diluted semen was frozen as described above and stored in liquid nitrogen until in vitro fertilization.

Thus, two types of straws were used: control straws and straws containing clofilium (0.2 μM). Straws were thawed in a water-bath at 37° C. for 45 s. Each straw was wiped with 70° ethanol before opening. The 0.25 mL thawed semen from control straw was layered under 4 mL of Sp-TALP capacitation medium in a 15 mL conical tube. The 0.25 mL thawed semen from clofilium straw was layered under 4 mL of Sp-TALP capacitation medium containing clofilium 0.2 μM in a 15 mL conical tube.

Sperm was centrifuged and resuspended in 200 μL Sp-TALP capacitation medium with or without clofilium (0.2 μM). Sperm was stored at 37° C. under saturated humidity for 0 h or 24 h.

Spermatozoa presenting a VCL>150 μm/s were selected and their motility was measured using CASA, performed as above in control condition or in the presence of clofilium.

The results are shown in FIG. 8, which illustrates the impact of clofilium on bovine sperm motility (in terms of VCL, in μm/s), the sperm presenting a sufficient velocity (VCL>150 μm/s), sperm being incubated 0 h or 24 h in a capacitation medium prior CASA evaluation, for each of the solutions tested (control or 0.2 μM clofilium).

In FIG. 8, "NS" means "Non-Significant".

FIG. 8 clearly shows that in the presence of clofilium for 24 hours in the capacitation medium, the subpopulation of sperm with VCL>150 μm/s has a higher mean velocity. Therefore, the motility of this sperm incubated during 24 hours in capacitation medium with clofilium is improved.

Example 5: Impact of Quinidine Treatment on Mouse Sperm Lifespan

Another inhibitor of the potassium channel was tested: quinidine.

The test related to the ability of mouse sperm to fertilize oocytes, sperm being incubated prior fertilization in a medium containing quinidine with regard to a control medium, without quinidine.

The control medium was the M16-BSA medium containing the sperm ("control"). It was compared to the same medium further including quinidine, at various concentrations 5 μM quinidine ("5 μM quinidine"), 10 μM quinidine ("10 μM quinidine"), 25 μM quinidine ("25 μM quinidine") and 100 μM quinidine ("100 μM quinidine").

The results are shown in FIG. 9, which illustrates the percentage of 2-cell embryos vs mature oocytes at 24 h post fertilization by mouse sperm for each of the solutions tested (as explained above).

It was observed that the sperm incubated during 12 hours with 25 μM quinidine has a better lifespan than the non-treated (i.e. control) sperm.

The invention claimed is:

1. An artificial insemination instrument for use in artificial insemination of an animal, comprising:

an artificial insemination straw comprising:

a substantially cylindrical tube; and a liquid-tight stopper arranged within the substantially cylindrical tube; and animal sperm within the substantially cylindrical tube, between the liquid-tight stopper and an end of the tube, in contact with an inhibitor of Slo3 potassium channel that improves ability of the animal sperm to fertilize said animal.

2. An artificial insemination instrument according to claim 1, wherein the artificial insemination instrument is a semen straw for cryopreservation.

3. A method for increasing life span or motility of animal sperm using an inhibitor of Slo3 potassium channel, comprising:

providing an artificial insemination instrument for use in artificial insemination of an animal, comprising animal sperm in contact with the inhibitor of Slo3 potassium channel; and inseminating said animal using the artificial insemination instrument;

wherein the inhibitor of Slo3 potassium channel improves ability of the animal sperm to fertilize said animal.

* * * * *